(12) United States Patent
Weber et al.

(10) Patent No.: US 9,504,804 B2
(45) Date of Patent: Nov. 29, 2016

(54) VARIABLE STIFFNESS SHAFT

(71) Applicant: BOSTON SCIENTIFIC SCIMED, INC.

(72) Inventors: Jan Weber, Maastricht (NL); Tracee E. J. Eidenschink, Wayzata, MN (US)

(73) Assignee: BOSTON SCIENTIFIC SCIMED INC., Maple Grove, MN (US)

( * ) Notice: Subject to any disclaimer, the term of this patent is extended or adjusted under 35 U.S.C. 154(b) by 0 days.

(21) Appl. No.: 14/523,866

(22) Filed: Oct. 25, 2014

(65) Prior Publication Data

US 2015/0196734 A1 Jul. 16, 2015

Related U.S. Application Data

(63) Continuation of application No. 11/280,120, filed on Nov. 16, 2005, now Pat. No. 8,876,772.

(51) Int. Cl.
| | | |
|---|---|---|
| *A61M 25/00* | (2006.01) | |
| *A61L 29/04* | (2006.01) | |
| *A61L 29/14* | (2006.01) | |
| *A61B 17/00* | (2006.01) | |
| *A61M 25/09* | (2006.01) | |

(52) U.S. Cl.
CPC ......... *A61M 25/0054* (2013.01); *A61L 29/041* (2013.01); *A61L 29/14* (2013.01); *A61M 25/0045* (2013.01); *A61B 2017/00398* (2013.01); *A61B 2017/00871* (2013.01); *A61M 2025/006* (2013.01); *A61M 2025/0058* (2013.01); *A61M 2025/0059* (2013.01); *A61M 2025/0063* (2013.01); *A61M 2025/0915* (2013.01); *A61M 2025/09133* (2013.01)

(58) Field of Classification Search
CPC ................ A61M 2025/0058; A61M 25/0054; A61M 25/0138; A61M 2025/0915; A61M 25/0158; A61M 25/0013
See application file for complete search history.

(56) References Cited

U.S. PATENT DOCUMENTS

| | | |
|---|---|---|
| 4,976,690 A | 12/1990 | Solar et al. |
| 5,095,915 A | 3/1992 | Engelson |
| 5,130,054 A | 7/1992 | Jasne |

(Continued)

FOREIGN PATENT DOCUMENTS

| | | |
|---|---|---|
| EP | 0132344 A2 | 1/1985 |
| WO | 9524236 A1 | 9/1995 |

(Continued)

OTHER PUBLICATIONS

All Non-Patent Literature documents and foreign patent documents have been previously uploaded in parent U.S. Appl. No. 11/280,120 filed Nov. 16, 2005.

(Continued)

*Primary Examiner* — Aarti B Berdichevsky
(74) *Attorney, Agent, or Firm* — Seager, Tufte & Wickhem LLP

(57) ABSTRACT

Medical devices may include structure or provision that permit a physician or other health care professional to adjust particular parameters such as flexibility, stiffness and compressive strength of at least a portion of the medical device. In some instances, the medical device may be adjusted prior to inserting the medical device into a patient. In some cases, the medical device may be adjusted while in use within the patient.

10 Claims, 11 Drawing Sheets

(56) References Cited

U.S. PATENT DOCUMENTS

| | | | |
|---|---|---|---|
| 5,437,288 A | 8/1995 | Schwartz et al. |
| 5,477,856 A | 12/1995 | Lundquist |
| 5,573,520 A | 11/1996 | Schwartz et al. |
| 5,605,543 A | 2/1997 | Swanson |
| 5,695,506 A | 12/1997 | Pike et al. |
| 5,746,701 A | 5/1998 | Noone |
| 5,797,856 A | 8/1998 | Frisbie et al. |
| 5,938,623 A | 8/1999 | Quiachon et al. |
| 6,001,068 A | 12/1999 | Uchino et al. |
| 6,004,279 A | 12/1999 | Crowley et al. |
| 6,160,084 A | 12/2000 | Langer et al. |
| 6,388,043 B1 | 5/2002 | Langer et al. |
| 6,428,489 B1 | 8/2002 | Jacobsen et al. |
| 6,514,237 B1 | 2/2003 | Maseda |
| 6,579,246 B2 | 6/2003 | Jacobsen et al. |
| 6,679,836 B2 | 1/2004 | Couvillon, Jr. |
| 6,766,720 B1 | 7/2004 | Jacobsen et al. |
| 6,786,876 B2 | 9/2004 | Cox |
| 6,835,173 B2 | 12/2004 | Couvillon, Jr. |
| 2003/0065373 A1 | 4/2003 | Lovett et al. |
| 2003/0068522 A1 | 4/2003 | Wang |
| 2003/0069522 A1 | 4/2003 | Jacobsen et al. |
| 2003/0114776 A1 | 6/2003 | Griffin et al. |
| 2003/0125709 A1 | 7/2003 | Eidenschink |
| 2003/0236445 A1 | 12/2003 | Couvillon, Jr. |
| 2004/0054322 A1 | 3/2004 | Vargas |
| 2004/0068161 A1 | 4/2004 | Couvillon, Jr. |
| 2004/0111044 A1 | 6/2004 | Davis et al. |
| 2004/0143160 A1 | 7/2004 | Couvillon, Jr. |
| 2004/0167437 A1 | 8/2004 | Sharrow et al. |
| 2004/0181174 A2 | 9/2004 | Davis et al. |
| 2005/0065456 A1 | 3/2005 | Eskuri |
| 2005/0085693 A1 | 4/2005 | Belson et al. |
| 2005/0102017 A1 | 5/2005 | Mattison |
| 2005/0107669 A1 | 5/2005 | Couvillon |
| 2005/0165439 A1 | 7/2005 | Weber et al. |

FOREIGN PATENT DOCUMENTS

| | | |
|---|---|---|
| WO | 9810694 A2 | 3/1998 |
| WO | 2005084750 A1 | 9/2005 |

OTHER PUBLICATIONS

Jager et al., "Microfabrication: conjugated polymer actuators", Science, vol. 290, No. 5496, pp. 1540-1545.

James et al, "Large field-induced strains in ferromagnetic shape memory materials", Materials Science and Engineering, vol. A273-275, 1999, pp. 320-325.

Sehitoglu et al., "Magnetization, shape memory and hysteresis behavior of single and polycrystalline FeNiCoTi", Journal of Magnatisim and Magnetic Materials, vol. 292, 2005,pp. 89-99.

Jager, "Actuator principle", http://www.ifm.liu.se/biorgel/research/micromuscles/principle.html, Aug. 3, 2005, 2 pgs.

VARIABLE STIFFNESS SHAFT

RELATED APPLICATIONS

This application is a continuation of U.S. application Ser. No. 11/280,120, filed Nov. 16, 2005.

TECHNICAL FIELD

The invention relates generally to medical devices having or including elongate shafts and relates more particularly to medical devices having elongate shafts that provide adjustability in flexibility, stiffness or compressive strength.

BACKGROUND

Medical devices may be subject to a number of often conflicting performance requirements such as flexibility and strength. In some instances, improved flexibility may come at the expense of reduced strength. Increased strength may come at the expense of reduced flexibility. Because each patient is unique, there may be a unique balance of performance parameters such as flexibility and strength optimal for a particular patient. Moreover, the optimal balance of flexibility and strength for a particular patient may vary during a procedure, depending on vasculature encountered.

Therefore, a need remains for medical devices that can be adjusted in performance parameters such as flexibility, stiffness and compressive strength, particularly in situ.

SUMMARY

The invention pertains generally to medical devices that include structure or provision that permit a physician or other health care professional to adjust particular parameters such as flexibility, stiffness and compressive strength of at least a portion of the medical device. In some instances, the medical device may be adjusted while in use within the patient.

Accordingly, an example embodiment of the invention may be found in a medical device that includes a hypotube and structure or apparatus for changing the compressive strength of the hypotube. The hypotube includes a number of slots disposed within the hypotube.

Another example embodiment of the invention may be found in a medical device that includes a hypotube and an electroactive polymer sleeve that is disposed over the hypotube. The hypotube includes a number of slots disposed within the hypotube.

Another example embodiment of the invention may be found in a medical device that includes a hypotube having a slot. The slot has a first wall and an opposing second wall. An electroactive polymer is disposed on at least one of the first wall and the second wall.

Another example embodiment of the invention may be found in a medical device that includes a hypotube that has a number of slots and a lumen extending through the hypotube. A sleeve that includes a number of fingers formed within the sleeve is disposed over the hypotube.

Another example embodiment of the invention may be found in a medical device that includes a hypotube that has a slot formed within the hypotube, the slot including a first wall and an opposing second wall. An electroactive polymer is disposed on at least one of the first wall and the opposing second wall. An insulating layer is disposed about the hypotube, and a conductive pattern is disposed about the insulating layer.

Another example embodiment of the invention may be found in a medical device that includes a hypotube having a first section and a second section. The first section includes a first slot and the second section includes a second slot. An electroactive polymer is disposed within the first slot and within the second slot. An insulating layer is disposed about the hypotube. A conductive pattern is disposed about the insulating layer. The conductive pattern includes a first conductive section disposed proximate the first hypotube section and a second conductive section disposed proximate the second hypotube section.

Another example embodiment of the invention may be found in a medical device that includes a non-conductive hypotube having a slot disposed within the hypotube. The slot includes a first wall and an opposing second wall. An electroactive polymer is disposed on at least one of the first wall and the second wall. A first conductive apparatus or structure and a second conductive apparatus or structure are both disposed near the hypotube such that the second conductive apparatus or structure is electrically isolated from the first conductive apparatus or structure.

Another example embodiment of the invention may be found in a method of deploying a medical device using a deployment catheter. The deployment catheter includes an outer shaft and an inner shaft that is disposed within the outer shaft. The inner shaft includes a slotted hypotube and strength altering apparatus or structure disposed thereon. A medical device is positioned within the outer shaft adjacent a distal end of the inner shaft. The deployment catheter is advanced through a patient's vasculature to a desired site. The strength altering apparatus or structure is activated in order to increase the compressive strength of the inner shaft, and then the inner shaft is advanced relative to the outer shaft in order to deploy the medical device.

The above summary of the present invention is not intended to describe each disclosed embodiment or every implementation of the present invention. The Figures, Detailed Description and Examples which follow more particularly exemplify these embodiments.

BRIEF DESCRIPTION OF THE FIGURES

The invention may be more completely understood in consideration of the following detailed description of various embodiments of the invention in connection with the accompanying drawings, in which.

Figure 1:
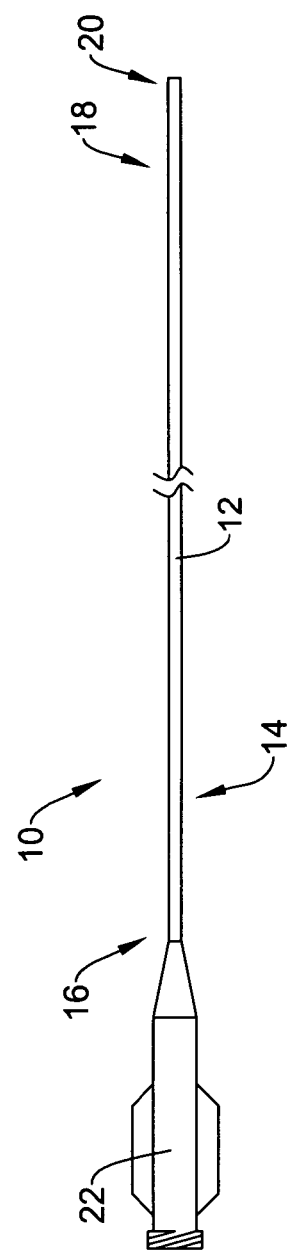
FIG. 1 is a side elevation view of a catheter in accordance with an embodiment of the invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following description should be read with reference to the drawings wherein like reference numerals indicate like elements throughout the several views. The drawings, which are not necessarily to scale, depict illustrative embodiments of the claimed invention.

FIG. 1 is a plan view of a catheter 10 in accordance with an embodiment of the present invention. The catheter 10 can be any of a variety of different catheters. In some embodiments, the catheter 10 can be an intravascular catheter. Examples of intravascular catheters include balloon catheters, atherectomy catheters, stent delivery catheters including catheters configured to deliver self-expanding stents, diagnostic catheters and guide catheters. The intravascular catheter 10 can be sized in accordance with its intended use. The catheter 10 can have a length that is in the range of about 50 to about 150 centimeters and can have any useful diameter. As illustrated, FIG. 1 portrays a guide catheter, but the invention is not limited to such. Except as described herein, the intravascular catheter 10 can be manufactured using conventional techniques.

In the illustrated embodiment, the intravascular catheter 10 includes an elongate shaft 12 that has a proximal region 14 defining a proximal end 16 and a distal region 18 defining a distal end 20. A hub and strain relief assembly 22 can be connected to the proximal end 16 of the elongate shaft 12. The hub and strain relief assembly 22 may largely be of conventional design and can be attached using conventional techniques, apart from being adapted to accommodate electrical contacts that are in electrical communication with the electrodes that will be discussed in greater detail with respect to subsequent Figures. In some instances, it is contemplated that hubs such as those used in electrophysiology catheters may be useful.

The elongate shaft 12 can include one or more shaft segments having varying degrees of flexibility. For example, the elongate shaft may include a relatively stiff proximal portion, a relatively flexible distal portion and an intermediate position disposed between the proximal and distal portions having a flexibility that is intermediate to both.

In some cases, the elongate shaft 12 may be formed of a single polymeric layer. In some instances, the elongate shaft 12 may include an inner liner such as an inner lubricious layer and an outer layer. In some cases, the elongate shaft 12 may include a reinforcing braid layer disposed between the inner and outer layers. The elongate shaft 12 is considered herein as generically representing a catheter to which various elements can be added to provide the catheter 10 with adjustable stiffness.

If the elongate shaft 12 includes an inner liner, the inner liner can include or be formed from a coating of a material having a suitably low coefficient of friction. Examples of suitable materials include perfluoro polymers such as polytetrafluoroethylene (PTFE), better known as TEFLON®, high density polyethylene (HDPE), polyarylene oxides, polyvinylpyrolidones, polyvinylalcohols, hydroxy alkyl cellulosics, algins, saccharides, caprolactones, and the like, and mixtures and combinations thereof. In some instances, a polymer such as PEBAX® may be used in conjunction with a hydrophilic and/or a hydrophobic coating.

The elongate shaft 12 can include, as an outer layer or layers, any suitable polymer that will provide the desired strength, flexibility or other desired characteristics. Polymers with low durometer or hardness can provide increased flexibility, while polymers with high durometer or hardness can provide increased stiffness. In some embodiments, the polymer material used is a thermoplastic polymer material. Some examples of suitable materials include polyurethane, elastomeric polyamides, block polyamide/ethers (such as PEBAX®), silicones, and co-polymers. The outer polymer layer 32 can be a single polymer, multiple longitudinal sections or layers, or a blend of polymers.

By employing careful selection of materials and processing techniques, thermoplastic, solvent soluble, and thermosetting variants of these materials can be employed to achieve the desired results. In some instances, a thermoplastic polymer such as a co-polyester thermoplastic elastomer, for example, available commercially under the ARNITEL® name, can be used. In some instances, a thermoplastic polymer may include micro-sized or even nano-sized fillers. Examples of suitable fillers include metallic fibers, ceramic fibers, nano clays, and carbon structures such as carbon fibers and carbon tubes.

Figure 2:
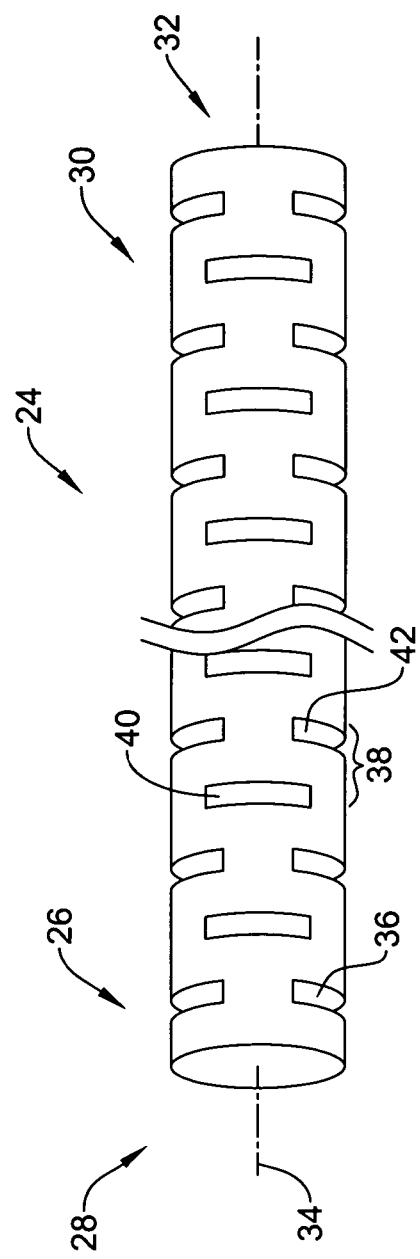
FIG. 2 is a perspective view of a hypotube in accordance with an embodiment of the invention.

FIGS. 2 through 20 illustrate various hypotubes in accordance with particular embodiments of the invention. The catheter 10 may be considered as including or being formed from any of the hypotubes described hereinafter. In particular, FIG. 2 illustrates a micromachined hypotube while FIGS. 3 through 20 illustrate modifications and/or additions to the micromachined hypotube of FIG. 2. It should be noted that while the invention is discussed herein with respect to catheters, the hypotubes described herein are equally applicable to other medical devices such as guidewires.

FIG. 2 illustrates a micromachined hypotube 24 having a proximal region 26 defining a proximal end 28 and a distal region 30 defining a distal end 32. The micromachined hypotube 24 can be seen as having an axial axis 34 extending the length of the hypotube 24. A number of slots 36 are disposed along the length of the micromachined hypotube 24. In the illustrated embodiment, the slots 36 are arranged at least substantially perpendicular to the axial axis 34. In other instances, the slots 36 may be arranged at an angle with respect to the axial axis 34.

While not illustrated, it is contemplated that at least some of the slots 36 may extend longitudinally. Moreover, it is contemplated that the dimensions of the slots 36, either length and/or width, may vary with respect to relative position along the hypotube 24. In some cases, the slot density, or number of slots per unit length of hypotube 24, may vary with respect to relative position along the hypotube 24. In some cases, one or more of the slots 36 may extend spirally about the hypotube 24.

Each of the slots 36 extend only partially around the circumference of the micromachined hypotube 24. In some instances, an individual slot 36 may extend about half way around the circumference of the micromachined hypotube 24. In other cases, an individual slot 36 can extend more than halfway around, if for example, increased flexibility is of highest importance. Conversely, if it is desired to provide additional column strength, perhaps with a certain sacrifice in flexibility, it is contemplated that each individual slot 36 may extend less than halfway around the micromachined hypotube 24.

It can be seen that individual slots 36 may be considered as being in pairs 38, with a pair 38 including a first slot 40 and a second slot 42. In some embodiments, as illustrated, the first slot 40 can have a first radial position on the micromachined hypotube 24 while the second slot 42 occupies a second radial position that is rotated from the first radial position. In some embodiments, as illustrated, the second slot 42 can be rotated about 90 degrees from the first slot 40. In other instances, the radial rotation can vary, especially if, for example, first slot 40 and second slot 42 are either longer or shorter than the illustrated length.

The micromachined hypotube 24 may be formed of any suitable material. In some instances, the micromachined hypotube 24 may be formed of a metallic material such as stainless steel or a nickel-titanium alloy such as Nitinol. The micromachined hypotube 24 may also be formed of any suitably stiff non-metallic material, such as carbon fiber or a stiff polymer such as polyimide.

The micromachined hypotube 24 may be formed having any desired length, width, material thickness, and slot size as required to satisfy the requirements of any particular application. Additional details concerning micromachined hypotube 24, including the manufacture thereof, can be found, for example, in U.S. Pat. No. 6,766,720 and published U.S. Patent Application No. 2004/0181174A2, each of which are fully incorporated, in their entirety, by reference herein.

Figure 4:
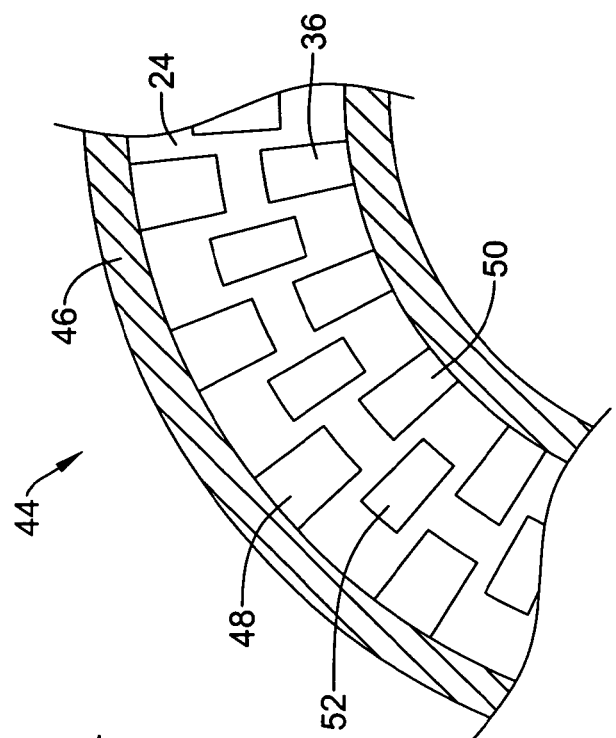
FIG. 4 is a view of the hypotube of FIG. 3.
Figure 3:
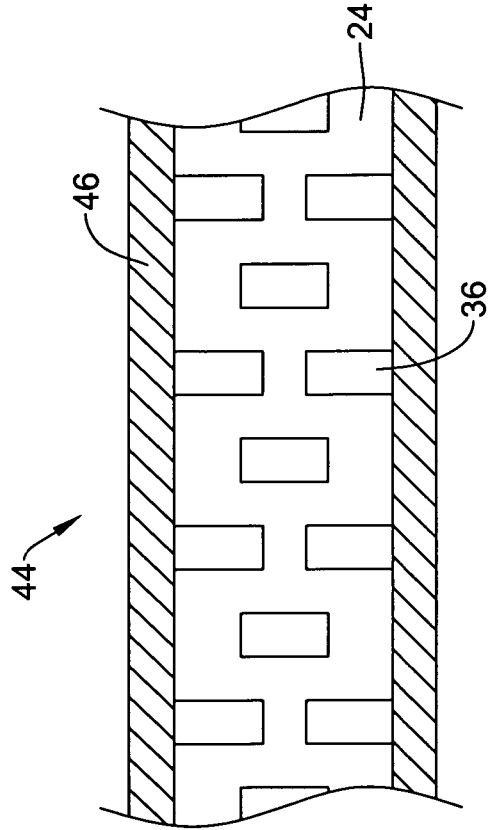
FIG. 3 is a side elevation view of a portion of a hypotube in accordance with an embodiment of the invention.

FIGS. 3 and 4 show an assembly 44 that includes a sleeve 46 disposed about the hypotube 24. The hypotube 24 includes a plurality of slots 36, as discussed above with respect to FIG. 2. In FIG. 3, the hypotube 24 is seen in a straight configuration while in FIG. 4, the hypotube 24 has undergone a certain amount of bending as a result of a force being applied to the hypotube 24.

As a result of being temporarily deformed into a bent configuration, the hypotube 24 can be seen as including expanded slots 48 along the outer perimeter, compressed slots 50 along the inner perimeter and unchanged slots 52 within the middle of the hypotube 24. It should be noted in FIG. 4 that the sleeve 46 has bent with the hypotube 24 and thus does not impact or at least does not substantially impact the flexibility of the hypotube 24.

The sleeve 46 may be formed of any suitable polymeric or metallic material. In some instances, the sleeve 46 may be formed of an electroactive polymer which can, when subjected to a potential difference, accommodate ions which may cause the electroactive polymer to swell. In some cases, the sleeve 46 may be formed of a shape memory material such as a shape memory metal or a shape memory polymer. Shape memory materials are known that can change from one configuration to another configuration upon a change in temperature, application of a magnetic field, light, or other suitable stimuli.

Figure 5:
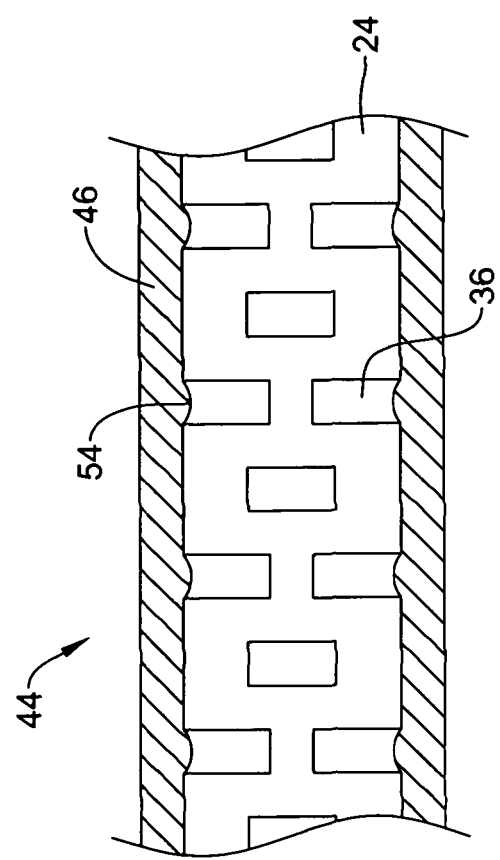
FIG. 5 is a view of the hypotube of FIG. 3.

In FIG. 5, the assembly 44 includes a sleeve 46 that has been changed into an activated configuration in which portions 54 of the sleeve 46 extend at least partially into the slots 36. As a result, the compressive strength of the hypotube 24 has been temporarily increased, as the portions 54 will reduce the amount of compression that slots 36, and thus the hypotube 24, can undergo.

The sleeve 46 can be considered as being convertible between an un-activated configuration, such as that shown in FIGS. 3 and 4, and an activated configuration as shown in FIG. 5. If the sleeve 46 is formed of some shape memory materials, the conversion from un-activated configuration to activated configuration may be permanent. However, in some instances, the sleeve 46 may also be returned to its un-activated configuration or even held at an intermediate configuration.

In particular, if the sleeve 46 is formed of an electroactive polymer, halting the potential difference being applied to the electroactive polymer will permit ions already within the polymer to remain there, but additional ions will not enter. Reversing the potential difference will cause the previously entered ions to exit the polymer. It should be recognized, therefore, that if sleeve 46 is formed of an electroactive polymer, the relative amount of ions entering or exiting the electroactive polymer may be controlled by controlling the potential difference applied to the electroactive polymer. Thus, the relative stiffness of the hypotube 24, to which sleeve 46 has been applied, may be adjusted on a continuous scale.

As noted, in some instances, an electroactive polymer may be employed with hypotubes in accordance with certain embodiments of the invention. In short, an electroactive polymer is a doped polymer that undergoes volume or configuration changes upon oxidation and reduction, such as may occur when the polymer is subjected to an electrical field driving the ions into or out of the polymer. Oxidation and reduction may cause ions to be either inserted into the polymer, thereby increasing the volume of the polymer, or to be removed from the polymer, thereby decreasing its volume.

In some instances, an electroactive polymer may be doped with a large, immobile anion A− and may be positioned in contact with an electrolyte that includes a small mobile cation M+, in which case cations are inserted and de-inserted. The electroactive polymer, in this case, expands in volume in its reduced state (a negative potential). This can be represented as the following redox (oxidation-reduction) reaction:

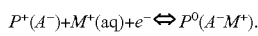

$$P^+(A^-)+M^+(aq)+e^- \Leftrightarrow P^0(A^-M^+).$$

In some instances, the electroactive polymer can be polypyrrole that has been doped with dodecyl benzene sulfonate (DBS), and can be placed in contact with an aqueous electrolyte of 0.1 molar NaDBS (sodium dodecyl benzene sulfonate). In this case, DBS is the large, immobile anion and Nat, possibly hydrated, is the small cation that is inserted and or de-inserted into the polymer. During reduction, sodium cations move into the polypyrrole to achieve charge neutrality within the polypyrrole. On oxidation, conversely, the sodium cations are expelled from the polypyrrole.

Polypyrrole and NaDBS have the following chemical structures, respectively:

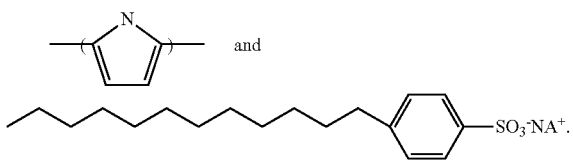

As noted, sodium cations can be provided by contacting the polypyrrole with an NaDBS electrolyte solution. However, in some instances, any variety of different aqueous salt solutions are useful. In particular, bodily fluids such as blood plasma and urine are effective.

Thus, in some instances, the electroactive polymer may be adapted to accommodate ions from an electrolyte solution provided within the hypotube 24. In some cases, the electroactive polymer may be adapted to accommodate ions from a patient's own blood. Ions in general, and particularly cations, may flow (as a result of an appropriate potential difference) from either an electrolyte solution such as NaDBS or from a patient's blood into the electroactive polymer, thereby swelling or otherwise activating the electroactive polymer.

As noted, it is useful to provide a voltage or potential difference in order to drive the redox reaction discussed above. The oxidized state, in which the sodium cations have been expelled or at least largely expelled from the polypyrrole, can be achieved at a voltage of 0 volts, i.e. no applied current. The reduced state, in which the sodium cations have moved into the polypyrrole, can be achieved, for example, at a voltage of about 1 volts, or perhaps about 1.2 volts. It should be noted that intermediate voltages, say in the range of 0.4 to 0.6 volts, can cause an intermediate level of volume increase as a result of cations migrating into the polymer. Depending on the voltage applied, the polypyrrole may achieve a volume increase of at least about 30 percent.

Depending on how the electroactive polymer is employed, in some cases moving from the oxidized state to the reduced state, via application of an appropriate potential difference across the electroactive polymer, simply causes a volume increase, and the electroactive polymer merely swells or grows. In some cases, the electroactive polymer may be coupled with an electrode, such as in a gold/polypyrrole bilayer, and moving between oxidized and reduced states may cause the bilayer to either bend or straighten.

As noted, in some instances, shape memory material may be employed with hypotubes in accordance with certain embodiments of the invention. In short, a shape memory material (either polymeric or metallic) is a material that can be moved or converted between two or more distinct configurations by application of an appropriate stimuli. In some instances, a structure or apparatus formed of a shape memory material may have an un-activated configuration and a remembered activated configuration, as will be discussed subsequently with respect to certain Figures.

Some shape memory materials, such as shape memory metals and shape memory polymers, can be moved between configurations via an appropriate temperature change. Suitable shape memory metals include the nickel-titanium alloys better known as nitinol. In some embodiments, nitinol alloys can include in the range of about 50 to about 60 weight percent nickel, with the remainder being essentially titanium. It should be understood, however, that in other embodiment, the range of weight percent nickel and titanium, and or other trace elements may vary from these ranges. Within the family of commercially available nitinol alloys, are categories designated as "superelastic" (i.e. pseudoelastic) and "linear elastic" which, although similar in chemistry, exhibits distinct and useful mechanical properties. In some instances, the sleeve 46 may include or be formed from nitinol.

In broad terms, shape memory polymers behave similarly to shape memory alloys such as the nickel-titanium alloys commonly referred to as Nitinol. The material is formed in its parent shape and is heated to a temperature that is at or above the glass transition temperature of the material. After the material has cooled, perhaps to ambient temperature, the material can be molded into any desired shape that is within the mechanical limitations of the material. This shape is temporarily retained until the material is once again subjected to its transition temperature. If desired, this process of low temperature deformation followed by thermally induced recovery of the parent shape can be repeated indefinitely.

One feature of shape memory polymers is that they have a large and reversible change in the modulus of elasticity of the material between the lower temperature glassy (crystalline) region and the higher temperature rubbery (elastic) region. In some embodiments, this large change in elasticity can be represented by a ratio of modulus of elasticity (below $T_g$) to modulus of elasticity (above $T_g$) of at least about 20.

In one aspect, shape memory polymers can be considered as having hard segments that are typically crystalline in nature, and soft segments that are typically amorphous in nature. However, some hard segments can be amorphous, and some soft segments can be crystalline. In this, segment refers to a block or sequence of the polymer that forms part of the shape memory polymer.

The terms hard segment and soft segment are relative in nature, and refer to differences in the transition temperatures of the segments, with a hard segment having the higher transition temperature. A shape memory polymer can have a first set of soft segments having a first transition temperature, and a second set of soft segments having a different, second transition temperature. In this case, the shape memory polymer can remember two distinct shapes that will be retrieved at different temperatures. The nature of shape memory polymers is discussed in greater detail in U.S. Pat. Nos. 6,160,084 and 6,388,043, each of which are incorporated in their entirety by reference herein.

In another aspect, the characteristics of shape memory polymers can be considered in terms of Brownian motion. In particular, molecular chains can undergo micro-Brownian motion above the glass transition temperature, once the modulus of elasticity has dropped. As noted above, shape memory polymers are considered as exhibiting a large drop in the modulus of elasticity when heating through the glass transition temperature.

In the elastic or rubbery state, the material can be easily deformed via mechanical means. As a result of the deformation, the molecular chains will orient themselves in line with the tension. Subsequently lowering the temperature below the glass transition temperature of the material freezes the micro-Brownian motion and therefore locks the material in its deformed configuration. The material will retain its deformed configuration for as long as the material remains below the glass transition temperature of the material.

When the material is heated above the glass transition temperature, however, micro-Brownian motion begins again, and the molecular chains will move to reduce or eliminate the tension caused by the initial deformation. As a result, the material will regain its remembered shape.

To function as a shape memory polymer, it is advantageous that the material either be partially crystallized or include at least some crosslinking. It has been found, however, that even when the material is partially crystallized or crosslinked, it can still be melted and processed using conventional injection or extrusion molding equipment.

The transition temperature of a shape memory polymer can be adjusted by varying the ratio of polymers used to create the shape memory polymer. A variety of different polymers can be made to have shape memory characteristics. Examples of suitable polymers include polynorborene (available commercially from Nippon Zeon Company), trans-polyisoprene (available from Kuraray Company), styrene-butadiene (available from Ashahi Company) and polyurethane (available from Mitsubishi Heavy Industries).

Additional materials that can be used include poly L-D lactic copolymer, oligo caprylactone copolymer and poly cyclo-octine. These polymers can be used separately or in conjunction with other shape memory polymers. In embodiments where more than one shape memory polymer is used, it may be useful that the polymers be compatible and that the glass transitions are similar. In some instances, if one shape memory polymer is used, for example, in a proximal section while a second shape memory polymer is used in a distal section, compatibility may not be necessary.

Shape memory polymers typically have three-dimensional networks as interpolymer chain interactions are important in retaining stable shapes. Examples of interpolymer chain interactions include chain entanglement, chemical cross-linking, and crystal, aggregate or glassy state formation. Entanglement and crosslinking are permanent changes and are used for constructing the original shape, while the other chain interactions are thermally reversible and thus are used to maintain the temporary (deformed) shapes.

For example, polynorborene relies on entanglement for memorizing an original shape, while trans-polyisoprene and polyethylene rely on crosslinking for this purpose. Polyurethane and styrene-butadiene copolymer rely on the formation of micro crystals in remembering an original shape. With respect to maintaining a deformed (temporary) shape, polynorborene and polyurethane employ the formation of a glass state. Trans-polyisoprene, styrene-butadiene copolymer and polyethylene each rely on the formation of microcrystals.

As noted, in some instances, magnetic shape memory material may be employed with hypotubes in accordance with certain embodiments of the invention. In short, a magnetic shape memory material is a material that has magnetic properties and that can be moved or changed between two different configurations, or can exhibit strain, in response to applying or removing a magnetic field, or in response to a temperature change.

An example of a magnetic shape memory material that can exhibit shape memory strain in response to thermal cycling are single crystalline and polycrystalline FeNiCoTi. In a particular embodiment, a Fe-29Ni-18-Co-4Ti (weight percent) composition may be used. This material is unusual in that it exhibits shape memory behavior with an FCC (face centered cubic) austenitic structure. This material provides a relatively modest strain of about 2.5 percent.

An example of a magnetic shape memory material that can exhibit shape memory strain in response to an applied magnetic field are NiMnGa alloys. In a particular embodiment, a Ni-24 at % Mn 24.7 at % Ga composition may be used. This material provides a strain of about 5 percent in response to cyclic application of a magnetic field. The sleeve 46 may include a shape memory material such as a shape memory metal, a shape memory polymer or a magnetic shape memory material.

Figure 6:
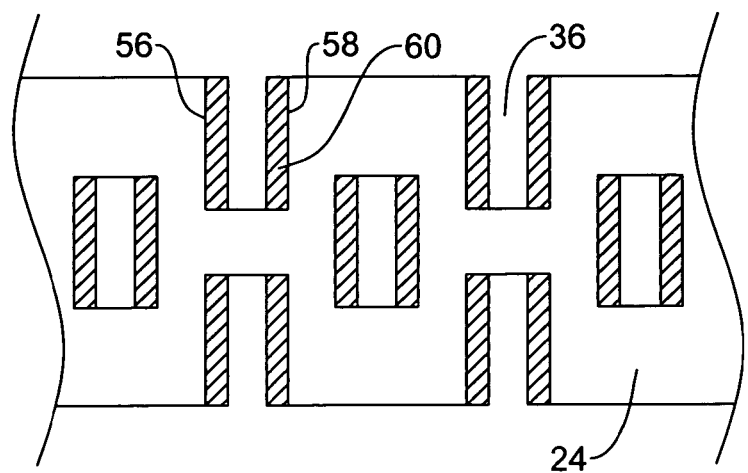
FIG. 6 is a side elevation view of a portion of a hypotube in accordance with an embodiment of the invention.

Returning now to the Figures, FIG. 6 shows a portion of the hypotube 24, including several slots 36. It can be seen that each of the slots 36 includes a first wall 56 and an opposing second wall 58. An electroactive polymer 60, such that those discussed above, is disposed on at least one of the first wall 56 and the second wall 58. As illustrated, the electroactive polymer 60 is evenly disposed on both the first wall 56 and the second wall 58.

While not expressly illustrated in FIG. 6, it will be appreciated that two electrodes will be provided in order to activate the electroactive polymer 60 by providing a potential difference between the two electrodes. If the hypotube 24 is metallic, the hypotube 24 itself may serve as one of the electrodes. In some instances, a conducting wire may be provided extending within an interior of the hypotube 24 to serve as the second electrode.

Figure 7:
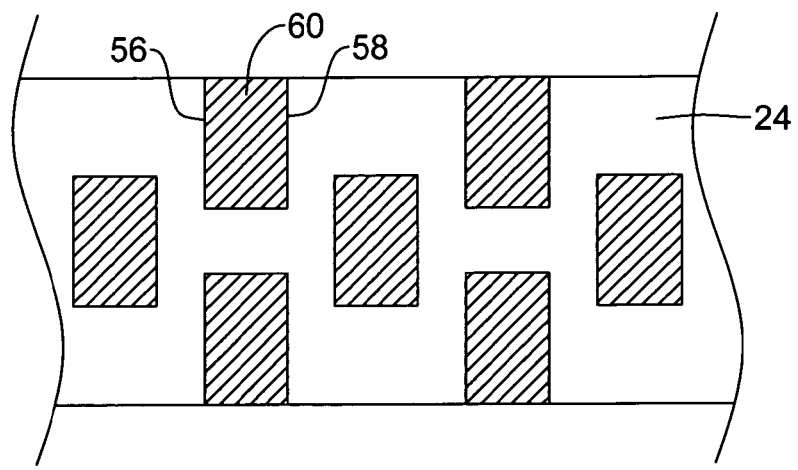
FIG. 7 is a side elevation view of a portion of a hypotube in accordance with an embodiment of the invention.

In FIG. 7, a potential difference has been supplied between the two (not illustrated) electrodes, thereby causing the electroactive polymer 60 to accept ions from an appropriate source, and thereby swell to fill at least a substantial portion of the slot 36. As a result, the compressive strength of the hypotube 24 has been increased.

Figure 8:
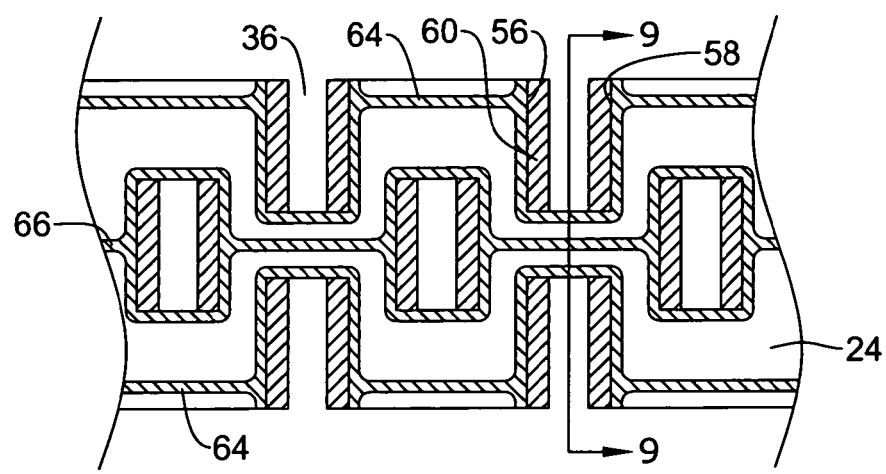
FIG. 8 is a side elevation view of a portion of a hypotube in accordance with an embodiment of the invention.
Figure 9:
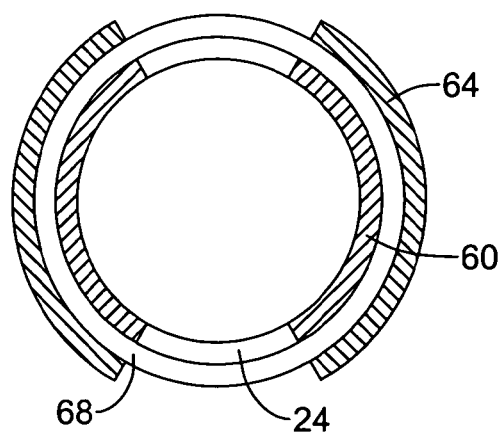
FIG. 9 is a cross-section of FIG. 8.

FIGS. 8 through 11 illustrate an embodiment in which a second electrode is provided on the surface of the hypotube 24. In FIG. 8, an assembly 62 includes the hypotube 24 as well as a first conductive pattern 64 and a second conductive pattern 66. In some instances, the hypotube 24 is electrically conductive and thus may serve as an electrode, with at least one of the first conductive pattern 64 and the second conductive pattern 66 serving as a second electrode. In some instances, as shown in FIG. 9, it may be useful to provide an insulating layer 68 over the hypotube 24, in order to electrically isolate the first conductive pattern 64 (and the second conductive pattern 66) from the hypotube 24.

Returning to FIG. 8, it is contemplated that the upper conductive pattern and the lower conductive pattern, both labeled as first conductive pattern 64, are electrically connected. In some instances, of course, it is contemplated that the first conductive pattern 64 may indeed be separated into electrically isolated and distinct upper and lower conductive patterns. In some instances, the second conductive pattern 66 is electrically isolated from the first conductive pattern 64. It is contemplated, of course, that the first conductive pattern 64 and the second conductive pattern 66 may, in some instances, be electrically connected to each other.

Each slot 36 includes, as discussed with respect to FIGS. 6 and 7, a first wall 56, an opposing second wall 58 and an electroactive polymer 60 disposed on at least one of first wall 56 and second wall 58. As seen in FIG. 8, no voltage has been applied between the first electrode and the second electrode, and thus the electroactive polymer 60 remains in an un-activated configuration.

Figure 10:
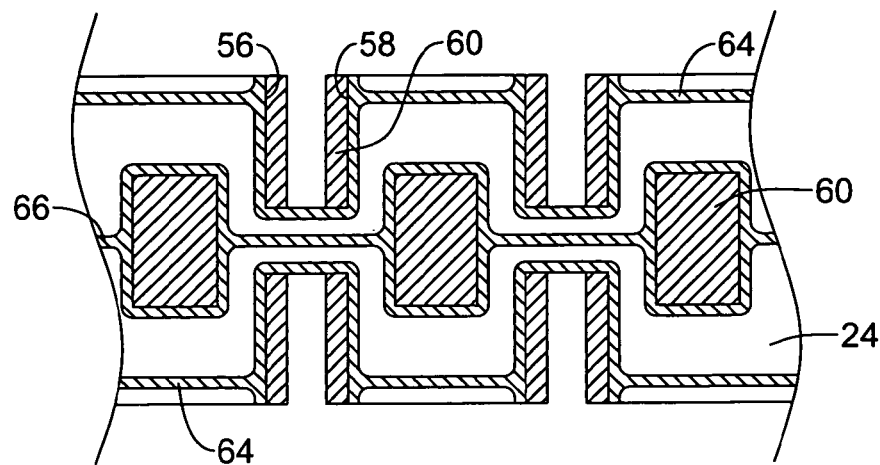
FIG. 10 is a view of the hypotube of FIG. 8.

In FIG. 10, however, it can be seen that a potential difference has been applied between the second conductive pattern 66 and another electrode, such as the hypotube 24 itself. In the slots 36 bounded by the first conductive pattern 64, the electroactive polymer 60 remains un-activated. However, in the slots 36 that are bounded by the second conductive pattern 66, the electroactive polymer 60 has absorbed available ions and has swelled to at least substantially fill the corresponding slots 36.

Figure 11:
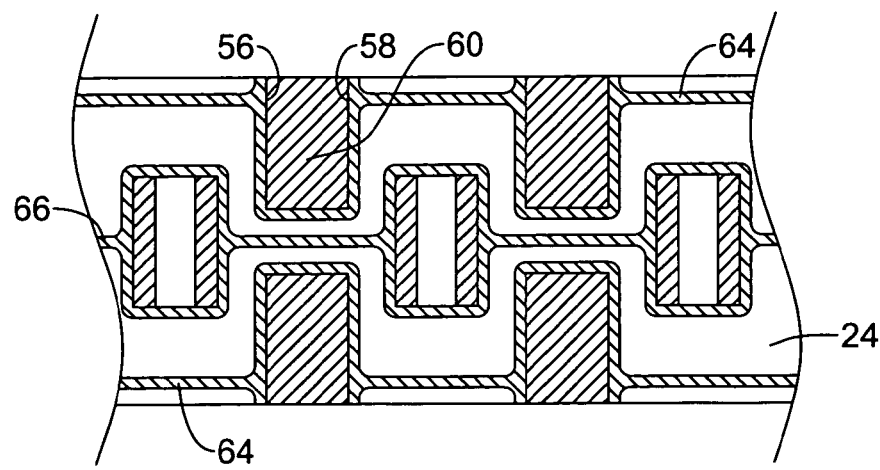
FIG. 11 is a view of the hypotube of FIG. 8.

In contrast, FIG. 11 shows an instance in which a potential difference has instead been applied between the first conductive pattern 64 and another electrode, such as the hypotube 24 itself. In the slots 36 bounded by the second conductive pattern 66, the electroactive polymer 60 remains un-activated. However, in the slots 36 that are bounded by the first conductive pattern 64, the electroactive polymer 60 has absorbed available ions and has swelled to at least substantially fill the corresponding slots 36.

It will be recognized that activating the electroactive polymer 60 within certain slots 36 while not activating the electroactive polymer 60 within other slots 36 may be useful in causing the hypotube 24 to bend. For example, activating the electroactive polymer 60 only within the slots 36 along a first side of the hypotube 24 can cause the hypotube 24 to bend in a direction opposite that of the first side of the hypotube 24. Activating the electroactive polymer 60 along two opposing sides will stiffen the hypotube 24 in a plane through the two opposing sides while permitting bending in a direction orthogonal to said plane. Adding more slots than those shown in the Figures will, of course, increase the options for controlled bending and adjustable stiffness.

Figure 12:
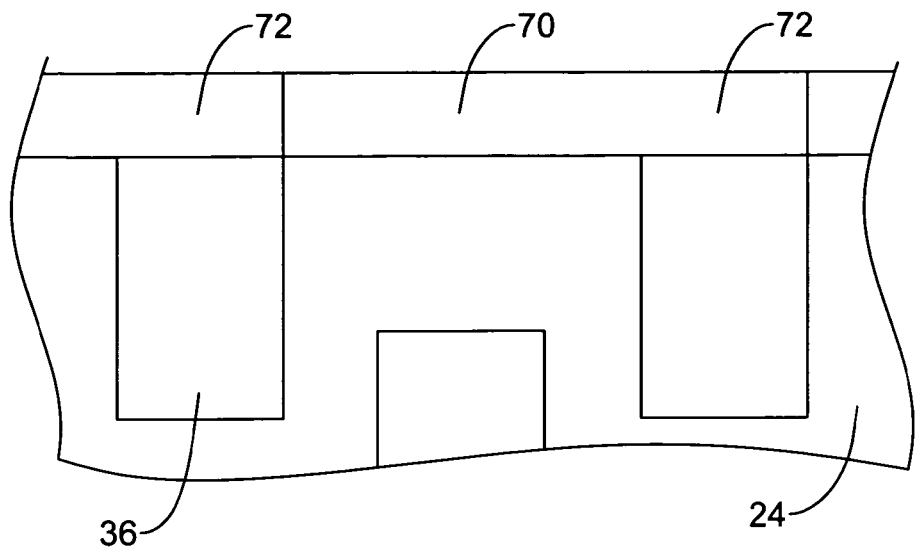
FIG. 12 is a side elevation view of a portion of a hypotube in accordance with an embodiment of the invention.
Figure 13:
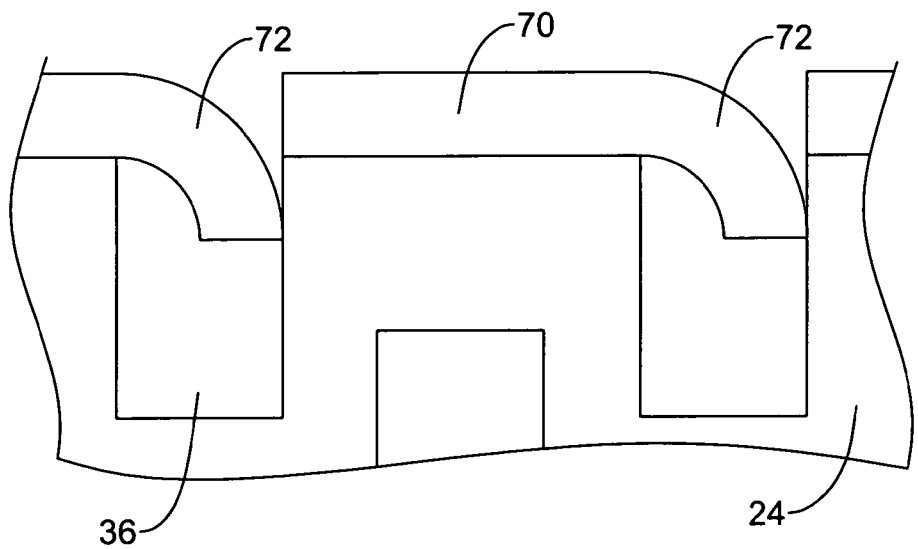
FIG. 13 is a view of the hypotube of FIG. 12.

FIGS. 12 and 13 illustrate an embodiment in which the hypotube 24 is provided with an exterior sleeve bearing fingers that may be activated into a position in which the fingers improve the compressive strength of the hypotube 24.

In particular, FIG. 12 shows a portion of the hypotube 24, bearing a sleeve 70. The sleeve 70 may be formed of any suitable material and includes fingers 72 that have an un-activated configuration (shown here in FIG. 12) in which the fingers 72 do not extend into, or at least do not extend substantially into, the slots 36. and an activated configuration, shown in FIG. 13, in which the fingers 72 extend at least partially into the slots 36 and thereby improve the compressive strength of the hypotube 24.

In some instances, the sleeve 70 and hence the fingers 72 may be a multilayer assembly including an electrode layer and an electroactive polymer layer disposed on one side or the other of the electrode layer. The electrode layer, if included, may be any suitable metal such as gold. If the hypotube 24 itself is used as an electrode, the sleeve 70 may also include an insulating layer disposed between the finger electrode layer and the hypotube 24.

Figure 14:
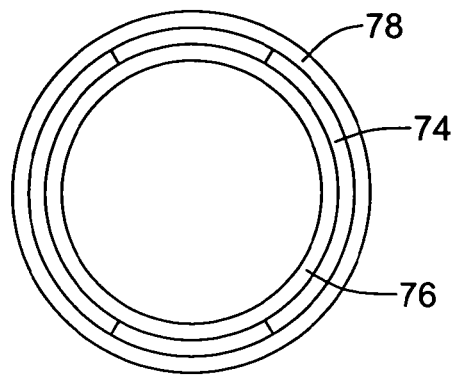
FIG. 14 is a diagrammatic end view of a portion of a hypotube in accordance with an embodiment of the invention.
Figure 15:
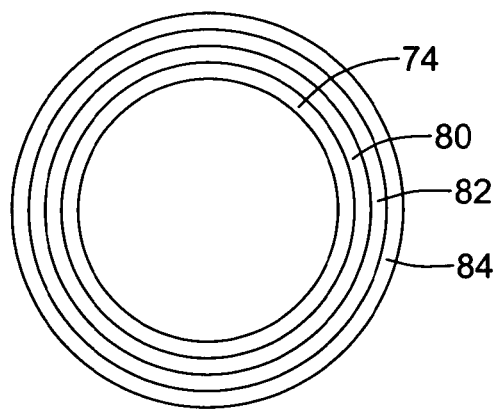
FIG. 15 is a diagrammatic end view of a portion of a hypotube in accordance with an embodiment of the invention.
Figure 16:
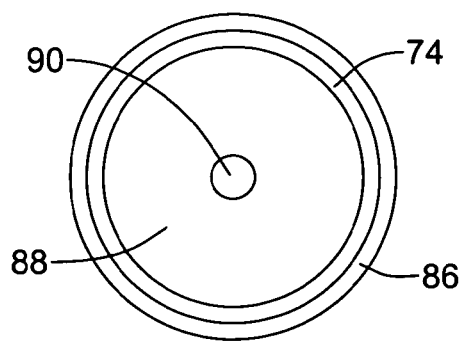
FIG. 16 is a diagrammatic end view of a portion of a hypotube in accordance with an embodiment of the invention.

FIGS. 14 through 16 diagrammatically illustrate particular embodiments of providing two electrodes, particularly if the hypotube 24 is non-conductive. It is contemplated that the hypotube 24 may be formed of any of a variety of non-conductive polymers.

In FIG. 14, a non-conductive hypotube 74 includes an inner conductive layer 76 formed within the interior of the hypotube 74 and an outer conductive layer 78 formed on the exterior of the hypotube 74. Each of the inner conductive layer 76 and the outer conductive layer 78 may simply be a metallic coating formed using any suitable technique such as dipping, spraying or the like. In some instances, the outer conductive layer 78 may be a patterned conductive layer, such as the first conductive layer 64 and/or the second conductive layer 66 shown in FIG. 8.

FIG. 15 illustrates an embodiment in which the hypotube 74 includes an inner conductive layer 80 formed on the exterior of the hypotube 74. An insulating layer 82, which may be formed of any suitable electrically-insulating material is disposed about the inner conductive layer 80. An outer conductive layer 84 is disposed about the insulating layer 82. The insulating layer 82 may be, for example, a diamond-like coating, an oxide, or a polymeric shrink tube. The outer conductive layer 84 may be formed of any suitable material using any suitable technique. For example, the outer conductive layer 84 may be formed of copper, using known photolithography techniques.

FIG. 16 shows an embodiment in which the hypotube 74 includes a conductive layer 86 that is disposed on the exterior of the hypotube 74. The conductive layer 86 may be formed of any suitable material using any suitable technique. A conductive wire 90 is disposed within the interior 88 of the hypotube 74. The conductive layer 86 may be a simple conducting layer, or it may be a conductive pattern as previously discussed. Similarly, the conductive wire 90 may be a simple copper wire exposed along its length, or the conductive wire 90 may have an insulating layer (not shown) having distinct gaps therein in order to direct current to desired locations.

Figure 17:
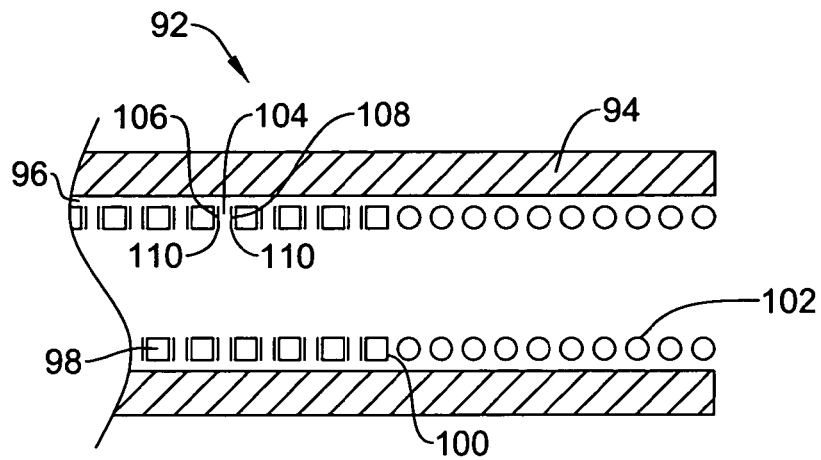
FIG. 17 is a side elevation view of a deployment catheter in accordance with an embodiment of the invention.
Figure 18:
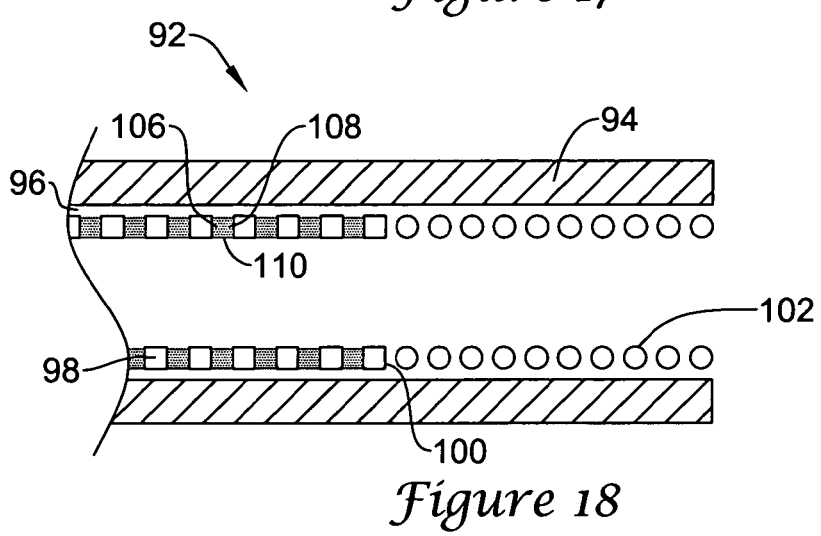
FIG. 18 is a view of the deployment catheter of FIG. 17.
Figure 19:
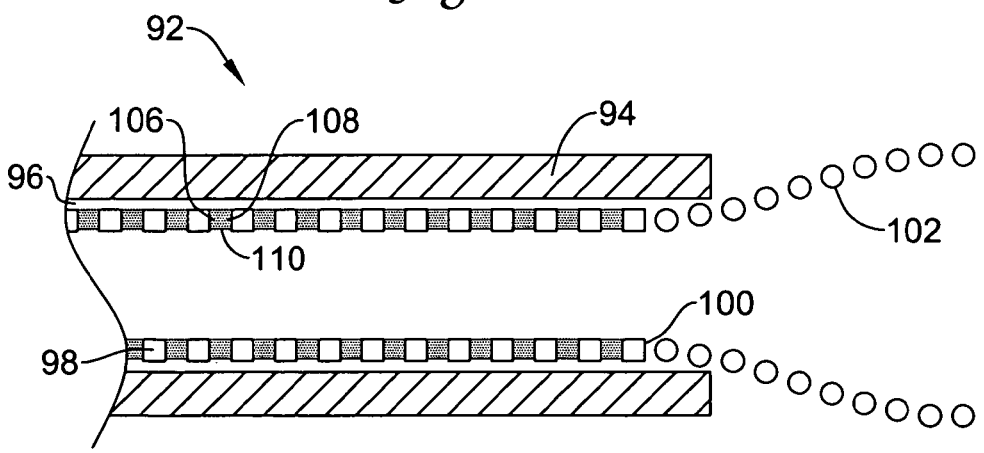
FIG. 19 is a view of the deployment catheter of FIG. 17.

FIGS. 17 through 19 illustrate a deployment catheter 92 in accordance with a particular embodiment of the invention. While deployment catheter 92 is illustrated herein as deploying a self-expanding stent, it should not be considered as being limited to such. Rather, deployment catheter 92 may be used to deploy a variety of medical devices such as stents, distal protection filters, vena cava filters, and other intravascular filters. In some ways, the deployment catheter 92 may be considered as an application for the hypotube 24 discussed previously herein.

In FIG. 17, the deployment catheter 92 may be seen as including an outer shaft 94 defining a lumen 96 and an inner shaft 98 disposed within the lumen 96. The outer shaft 94 may be of any suitable construction, and may be a single layer polymeric sheath. In some instances, of course, the outer shaft 94 may include multiple polymeric layers, reinforcing structures, and the like. The inner shaft 98 is a hypotube having a distal end 100. A stent 102 is positioned within the lumen 96, proximate the distal end 100 of the inner shaft 98.

As noted, the inner shaft 98 is a hypotube and includes a number of slots 104. Each slot 104 has a first wall 106 and an opposing second wall 108. An electroactive polymer 110 is disposed along the first wall 106 and a second wall 108. As seen, the electroactive polymer 110 is in an un-activated configuration, i.e. no potential difference has been applied. It is considered that this configuration may be preferable for advancing the deployment catheter 92 through a patient's vasculature.

Once a desired treatment site has been reached, it may be advantageous to apply a potential difference to the electroactive polymer 110, thereby causing available ions to enter and thus swell the electroactive polymer 110. As seen in FIG. 18, the electroactive polymer 110 has obtained its activated configuration in which the electroactive polymer 110 fills at least a substantial portion of the slot 104. As seen in FIG. 19, the stent 102 (or other deployable structure) may be deployed as a result of relative axial movement between the outer shaft 94 and the inner shaft 98.

Figure 20:
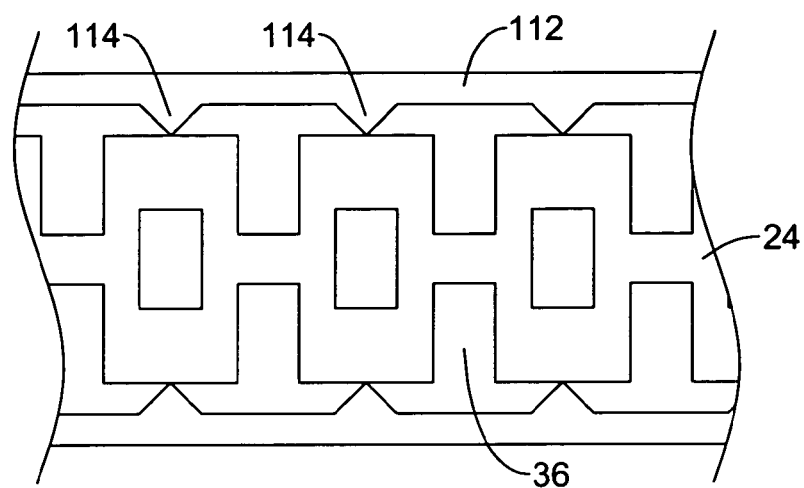
FIG. 20 is a side elevation view of a portion of a hypotube in accordance with an embodiment of the invention.
Figure 21:
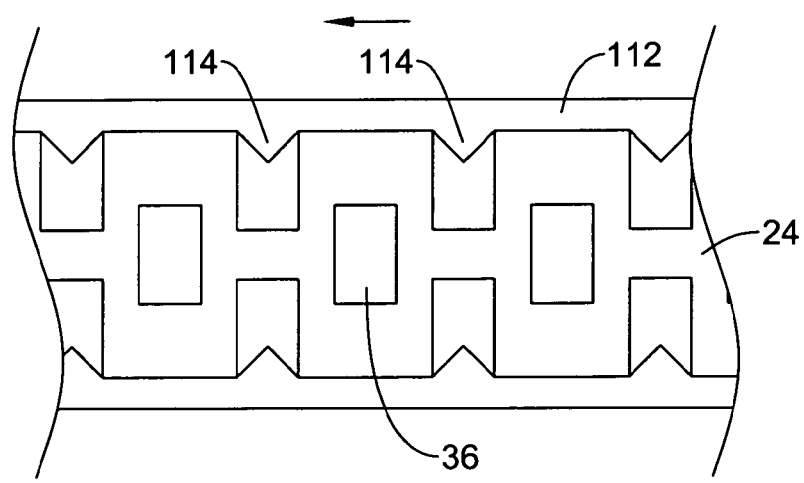
FIG. 21 is a view of the hypotube of FIG. 20.

In some instances, a hypotube 24 (FIG. 2) may achieve increased compressive strength through non-electrical methods. FIGS. 20 and 21 illustrate a mechanical solution to increasing compressive strength.

In FIG. 20, the hypotube 24 can be seen as including a number of slots 36. An apparatus 112 bearing a number of protrusions 114 is disposed about the hypotube 24. In FIG. 20, the apparatus 112 is in an un-activated configuration and is considered to be spring-loaded. Moving the apparatus 112 axially with respect to the hypotube 24 causes the protrusions 114 to move and thus enter the slots 36. Once the protrusions 114 enter the slots 36, the protrusions 114 limit how far the slots 36 may compress, and thereby improves the compressive strength of the hypotube 24.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

We claim:

1. A medical device comprising:
    a hypotube comprising a plurality of slots passing transversely through a longitudinal sidewall of the hypotube, each slot of the plurality of slots comprising a first wall and an opposing second wall defining a space between the first wall and the opposing second wall;
    an electroactive polymer sleeve disposed on an exterior wall of the hypotube, said electroactive polymer sleeve having a first configuration in which the electroactive polymer sleeve does not occupy the space between the first wall and the opposing second wall and a second configuration in which the electroactive polymer sleeve at least partially occupies the space between the first wall and the opposing second wall, which electroactive polymer when subjected to a potential difference applied between two electrodes causes available ions to move into the electroactive polymer to swell the electroactive polymer such that the electroactive polymer sleeve changes from the first configuration to the second configuration thereby changing a compressive strength of the hypotube;
    wherein the hypotube is one of the two electrodes.

2. The medical device of claim 1, wherein the electroactive polymer sleeve includes fingers such that each slot of the plurality of slots has a finger of the electroactive polymer sleeve aligned with the slot.

3. The medical device of claim 2, wherein the finger aligned with each slot at least partially occupies the space between the first wall and the opposing second wall of the slot in the second configuration.

4. The medical device of claim 3, wherein in the second configuration, a portion of each finger bends into the space between the first wall and the opposing second wall of the slot.

5. The medical device of claim 2, further comprising a second of the two electrodes disposed about the electroactive polymer sleeve.

6. The medical device of claim 5, wherein the second of the two electrodes disposed about the electroactive polymer sleeve consists of an electrode layer of a multi-layer electroactive polymer sleeve.

7. The medical device of claim 6, wherein each finger comprises the electrode layer and an electroactive polymer disposed on the electrode layer.

8. The medical device of claim 1, wherein the electroactive polymer sleeve comprises an electroactive polymer doped with an immobile anion.

9. The medical device of claim 8, wherein the electroactive polymer sleeve comprises polypyrrole.

10. The medical device of claim 8, wherein the immobile anion comprises sodium dodecyl benzene sulfonate.

* * * * *